(12) United States Patent
Riedel et al.

(10) Patent No.: US 10,173,017 B2
(45) Date of Patent: Jan. 8, 2019

(54) MEDICAMENT DELIVERY DEVICE WITH USE INDICATOR

(71) Applicant: SANOFI-AVENTIS DEUTSCHLAND GMBH, Frankfurt am Main (DE)

(72) Inventors: Stephan Riedel, Frankfurt am Main (DE); Steffen Raab, Frankfurt am Main (DE); Kerstine Hemmann, Frankfurt am Main (DE); Michael Caspers, Frankfurt am Main (DE); Katja Hoerhold, Frankfurt am Main (DE); Daniel Kerkow, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 333 days.

(21) Appl. No.: 14/435,564

(22) PCT Filed: Oct. 2, 2013

(86) PCT No.: PCT/EP2013/070582
§ 371 (c)(1),
(2) Date: Apr. 14, 2015

(87) PCT Pub. No.: WO2014/060214
PCT Pub. Date: Apr. 24, 2014

(65) Prior Publication Data
US 2015/0265782 A1    Sep. 24, 2015

(30) Foreign Application Priority Data

Oct. 15, 2012  (EP) .................................... 12188585

(51) Int. Cl.
*A61M 5/50*    (2006.01)
*A61M 5/32*    (2006.01)

(52) U.S. Cl.
CPC ........ *A61M 5/5086* (2013.01); *A61M 5/3202* (2013.01); *A61M 2005/3267* (2013.01); *A61M 2205/583* (2013.01); *A61M 2205/584* (2013.01)

(58) Field of Classification Search
CPC .... A61M 2005/3267; A61M 2205/583; A61M 2205/584; A61M 5/3202; A61M 5/5086
See application file for complete search history.

(56) References Cited

U.S. PATENT DOCUMENTS 5,591,189 A * 1/1997 Yoon .................. A61B 10/0233
604/164.12
2009/0227956 A1* 9/2009 Emmott ................ A61M 5/002
604/196

(Continued)

FOREIGN PATENT DOCUMENTS

CN         1856333        11/2006
CN         101014379       8/2007
(Continued)

OTHER PUBLICATIONS

Extended European Search Report in Application No. 12188585.9, dated May 8, 2013, 6 pages.

(Continued)

*Primary Examiner* — Brandy S Lee
(74) *Attorney, Agent, or Firm* — Fish & Richardson P.C.

(57) ABSTRACT

Described is a medicament delivery device (100, 200) comprising a case (105, 205) adapted to hold a container with a medicament and having a needle (300), a needle sleeve (120, 220) telescopically coupled to the case (105, 205) and having a first extended position relative to the case (105, 205) in which the needle (300) is covered, a retracted position relative to the case (105, 205) in which the needle (300) is exposed, and a second extended position relative to the case (105, 205) in which the needle is covered, a first (Continued)

indicia (125, 225) disposed on the needle sleeve (120, 220) which is visible in the first extended position and the second extended position, and a second indicia (130, 230) disposed on the needle sleeve (120, 220) and not visible in the first extended position and visible the second extended position.

18 Claims, 6 Drawing Sheets

(56) References Cited

U.S. PATENT DOCUMENTS

| | | | | |
|---|---|---|---|---|
| 2011/0066114 A1* | 3/2011 | McDown | ............ | A61M 5/3245 604/192 |
| 2013/0211338 A1* | 8/2013 | Roberts | ................. | A61M 5/326 604/198 |

FOREIGN PATENT DOCUMENTS

| | | |
|---|---|---|
| CN | 102176937 | 9/2011 |
| CN | 102470219 | 5/2012 |
| JP | 2010/501295 | 1/2010 |
| JP | 2011/512195 | 4/2011 |
| WO | WO 2009/102596 | 8/2009 |
| WO | WO 2009/114777 | 9/2009 |
| WO | WO 2011/92524 | 8/2011 |

OTHER PUBLICATIONS

International Preliminary Report on Patentability in International Application No. PCT/EP2013/070582, dated Apr. 21, 2015, 6 pages.
International Search Report and Written Opinion in International Application No. PCT/EP2013/070582, dated Oct. 29, 2013, 8 pages.
Rote Liste, "50. Hypophysen-, Hypothalamushormone, andere regulatorische Peptide u. ihre Hemmstoffe," Chapter 50, ed. 2008, 20 pages.
Japanese Office Action in Application No. 2015-536069, dated Jun. 27, 2017, 6 pages.
Chinese Search Report in Application No. 201380064739.2, dated Oct. 22, 2016, 2 pages.

* cited by examiner

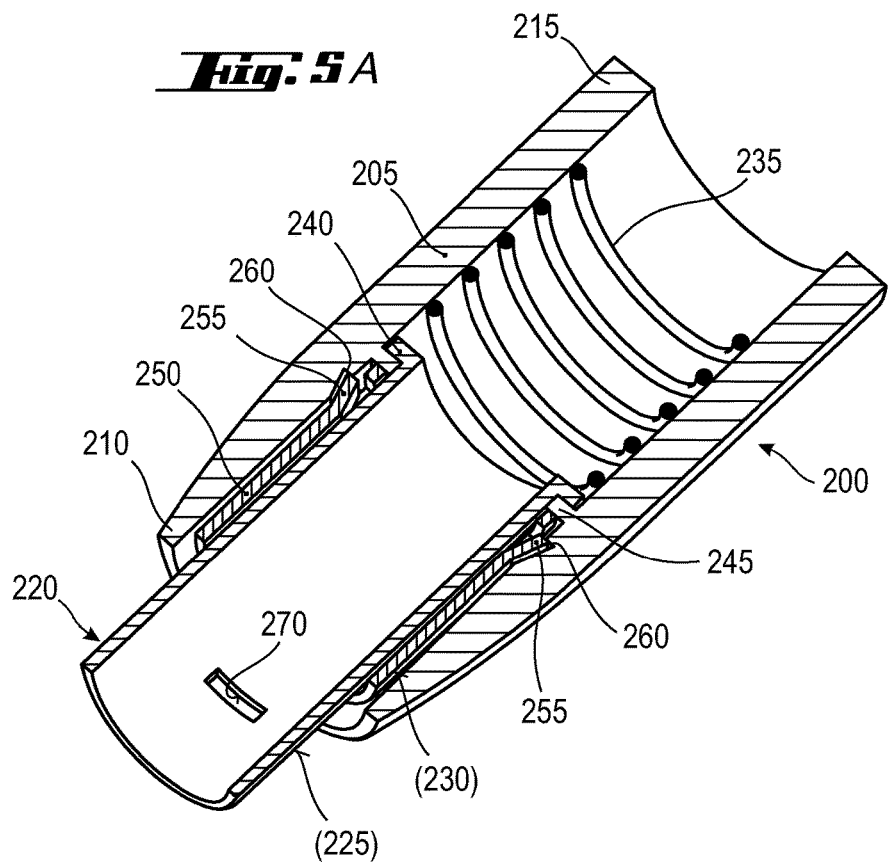
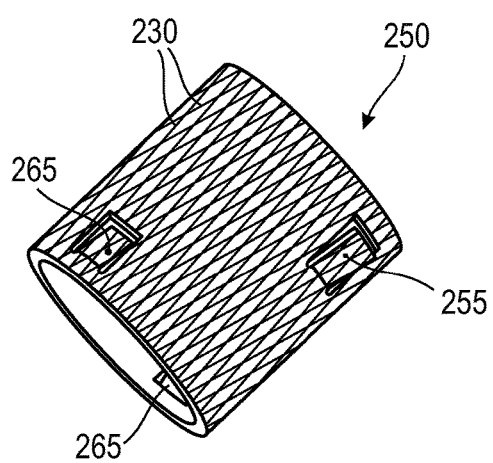

MEDICAMENT DELIVERY DEVICE WITH USE INDICATOR

This application is a 371 U.S. National Application of PCT/EP2013/070582, filed on Oct. 2, 2013, which claims priority to European Patent Application Nos. 12188585.9, filed on Oct. 15, 2012, the entire contents of which are incorporated herein by reference.

TECHNICAL FIELD

The invention relates to medicament delivery device with a use initiation indicator.

BACKGROUND OF THE INVENTION

Administering an injection is a process which presents a number of risks and challenges for users and healthcare professionals, both mental and physical. Injection devices typically fall into two categories—manual devices and auto-injectors. In a conventional manual device, manual force is required to drive a medicament through a needle. This is typically done by some form of button/plunger that has to be continuously pressed during the injection. There are numerous disadvantages associated with this approach. For example, if the button/plunger is released prematurely, the injection will stop and may not deliver an intended dose. Further, the force required to push the button/plunger may be too high (e.g., if the user is elderly or a child). And, aligning the injection device, administering the injection and keeping the injection device still during the injection may require dexterity which some patients (e.g., elderly patients, children, arthritic patients, etc.) may not have.

Autoinjector devices aim to make self-injection easier for patients. A conventional autoinjector may provide the force for administering the injection by a spring, and trigger button or other mechanism may be used to activate the injection. Autoinjectors may be single-use or reusable devices.

Conventional delivery devices may also have limited feedback mechanisms. For example, some conventional delivery devices may only provide an audible feedback when an injection is initiated. Thus, a patient may not be aware when the injection is complete. In this case, the patient may remove the delivery device during dose delivery which may lead to injury, pain, or incorrect dose delivery.

Thus, there remains a need for an improved medicament delivery device with a use indicator.

SUMMARY OF THE INVENTION

It is an object of the present invention to provide an improved medicament delivery device with a use indicator.

In an exemplary embodiment, a medicament delivery device according to the present invention comprises a case adapted to hold a container with a medicament and having a needle, a needle sleeve telescopically coupled to the case and having a first extended position relative to the case in which the needle is covered, a retracted position relative to the case in which the needle is exposed, and a second extended position relative to the case in which the needle is covered, a first indicia disposed on the needle sleeve that is visible in the first extended position and the second extended position, and a second indicia disposed on the needle sleeve that is not visible in the first extended position and is visible the second extended position.

In an exemplary embodiment, a distal end of the needle sleeve extends a first predetermined length beyond a distal end of the case in the first extended position and extends a second predetermined length beyond the distal end of the case in the second extended position, and the second predetermined length is greater than the first predetermined length. The first indicia is disposed on the first predetermined length of the needle sleeve, and the second indicia is disposed on the needle sleeve proximal of the first predetermined length.

In an exemplary embodiment, the medicament delivery device further comprises an indicator sleeve telescopically disposed in the case. The indicator sleeve has a proximal position relative to the case in which the indicator sleeve is not visible and a distal position relative to the case in which the indicator sleeve is visible. The indicator sleeve engages the needle sleeve when the needle sleeve is in the retracted position, and wherein the indicator sleeve translates from the proximal position to the distal position when the needle sleeve translates from the retracted position to the second extended position.

In an exemplary embodiment, the second indicia (230) is disposed on the indicator sleeve (250).

In an exemplary embodiment, the indicator sleeve includes one or more first resilient latches adapted to releasably engage one or more first notches in the case. The indicator sleeve includes one or more second resilient latches adapted to engage one or more second notches in the needle sleeve. The second latches engage the second notches when the needle sleeve is in the retracted position and the indicator sleeve is in the proximal position. The first latches disengage the first notches when the needle sleeve translates from the retracted position to the second extended position and the indicator sleeve translates from the proximal position to the distal position.

In an exemplary embodiment, a rib is disposed in the case to prevent proximal movement of the indicator sleeve from the proximal position.

In an exemplary embodiment, the medicament delivery device further comprises a spring biasing the needle sleeve away from the retracted position.

In an exemplary embodiment, the first indicia includes at least one of a first color, a first symbol, a first text and a first graphic, and the second indicia includes at least one of a second color, a second symbol, a second text and a second graphic.

In an exemplary embodiment, the needle sleeve is locked in the second extended position.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(02)25, Asp28] Exendin-4(1-39),
des Pro36 [Met(O)14 Trp(02)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2) 25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2) 25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains p and c have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein:

FIG. 5A shows another exemplary embodiment of a medicament delivery device with a delivery initiation indicator according to the present invention before use;

FIG. 5B shows an exemplary embodiment of an indicator sleeve according to the present invention;

Corresponding parts are marked with the same reference symbols in all figures.

DETAILED DESCRIPTION

Figure 1:
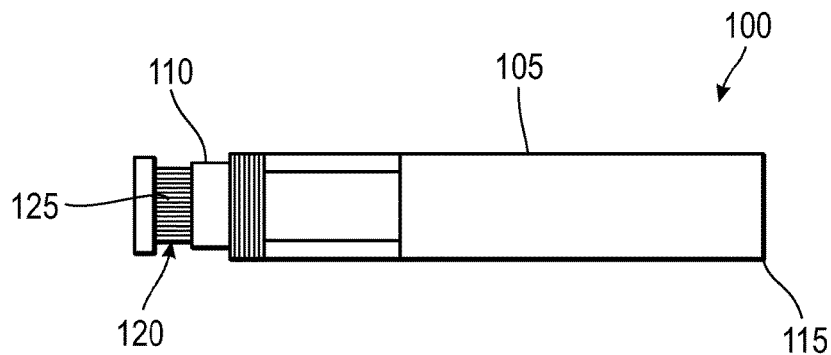
FIG. 1 shows an exemplary embodiment of a medicament delivery device with a delivery initiation indicator according to the present invention before use.

FIG. 1 shows an exemplary embodiment of a medicament delivery device 100 according to the present invention. The delivery device 100 may be any type of injection device which is used to inject a medicament from a syringe or cartridge. Those of skill in the art will understand that such injection devices include, but are not limited to, pen injectors, pre-filled syringes, autoinjectors, perfusion devices, infusion devices, etc.

In the exemplary embodiment shown in FIG. 1, the delivery device 100 includes a case 105 which may be a cylinder having an open distal end 110 and a closed proximal end 115. In another exemplary embodiment, a trigger button may be disposed on the proximal end 115. Telescopically coupled to the case 105 may be a needle sleeve 120. The needle sleeve 120 may be biased (e.g., by a spring) in a first extended position relative to the case 105 to ensure that a needle 300 on a syringe or cartridge in the delivery device 100 is covered prior to use. In the first extended position, a distal end of the needle sleeve 120 extends a first predetermined length beyond the distal end 110 of the case 105. In an exemplary embodiment, the first predetermined length includes a first indicia 125 such as, for example, a first color, a first symbol, a first text, a first graphic, etc. or any combination thereof. For example, the first indicia 125 may be the color green. When the needle sleeve 120 is in the first extended position, the first indicia 125 may be visible to a patient and indicate that the delivery device 100 has not been previously used and is ready for use.

Figure 2:
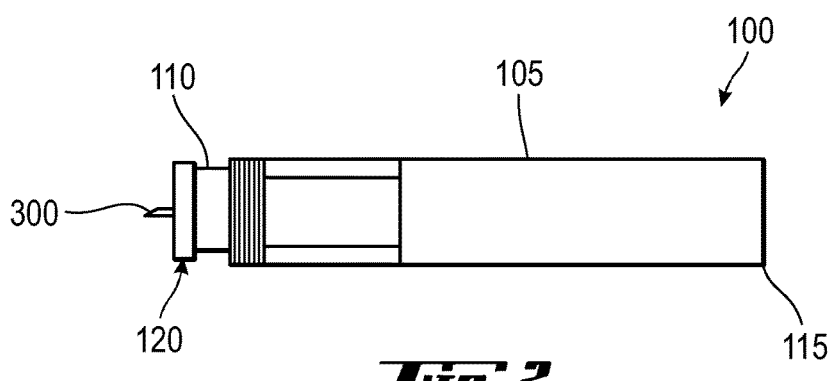
FIG. 2 shows an exemplary embodiment of a medicament delivery device with a delivery initiation indicator according to the present invention during use.

FIG. 1 shows an exemplary embodiment of the delivery device 100 prior to use. FIG. 2 shows an exemplary embodiment of the delivery device 100 during use, when the delivery device 100 has been placed on an injection site. As the delivery device 100 is placed on the injection site, the distal end of the needle sleeve 120 contacts the injection site, and continued distally directed force causes the needle sleeve 120 to move in the proximal direction relative to the case 105 against the biasing force. When the needle sleeve 120 translates in a proximal direction relative to the case 105 such that the first indicia 125 is substantially covered by the case 105, the needle sleeve 120 is in a retracted position. In an exemplary embodiment, when the needle sleeve 120 is in the retracted position, a distal end of a needle 300 may be exposed for insertion into the injection site, and an interlock mechanism may be activated which advances a plunger (under force of a compressed spring) into the syringe or cartridge to drive a stopper therein distally for expelling the medicament. In another exemplary embodiment, when the needle sleeve 120 has moved into the retracted position relative to the case 105, an interlock mechanism may be activated which advances the syringe or cartridge from a first proximal position to a second distal position for inserting the needle 300 into the injection site. The interlock mechanism may also cause advancement of the plunger into the syringe or cartridge to drive the stopper distally for expelling the medicament, or a trigger button may be pressed to release the plunger. In a further exemplary embodiment, when the needle sleeve 120 has moved into the retracted position relative to the case 105, an interlock mechanism may be activated which releases the trigger button, and when the trigger button is pressed the syringe or cartridge advances from a first proximal position to a second distal position for inserting the needle 300 into the injection site, and causes advancement of the plunger into the syringe or cartridge to drive the stopper distally for expelling the medicament.

Figure 3:
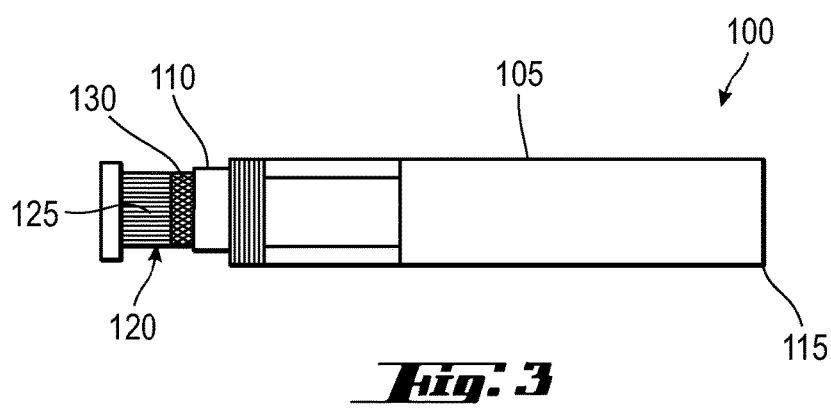
FIG. 3 shows an exemplary embodiment of a medicament delivery device with a delivery initiation indicator according to the present invention after use.

FIG. 3 shows an exemplary embodiment of the delivery device 100 after use, when the delivery device 100 has been removed from the injection site. Under the biasing force, the needle sleeve 120 translates distally relative to the case 105 to a second extended position relative to the case 105 in which the distal end of the needle sleeve 120 is a second predetermined length, greater than the first predetermined length, from the distal end 110 of the case 105. The second predetermined length of the needle sleeve 120 includes the first indicia 125 disposed on the first predetermined length and further includes a second indicia 130 on the needle sleeve 120 proximal of the first indicia 125. The second indicia 130 may be a second color, a second symbol, a second text, a second graphic, etc. or any combination thereof, which is/are different from the first indicia 125. For example, if the first indicia 125 is the color green, the second indicia 130 may be the color red. When the needle sleeve 120 is in the second extended position, the second indicia 130 may be visible to a patient and indicate that the delivery device 100 has been used and should not be used again.

In an exemplary embodiment, the needle sleeve 120 may be locked in the second extended position to prevent reuse of the delivery device 100.

Figure 4:
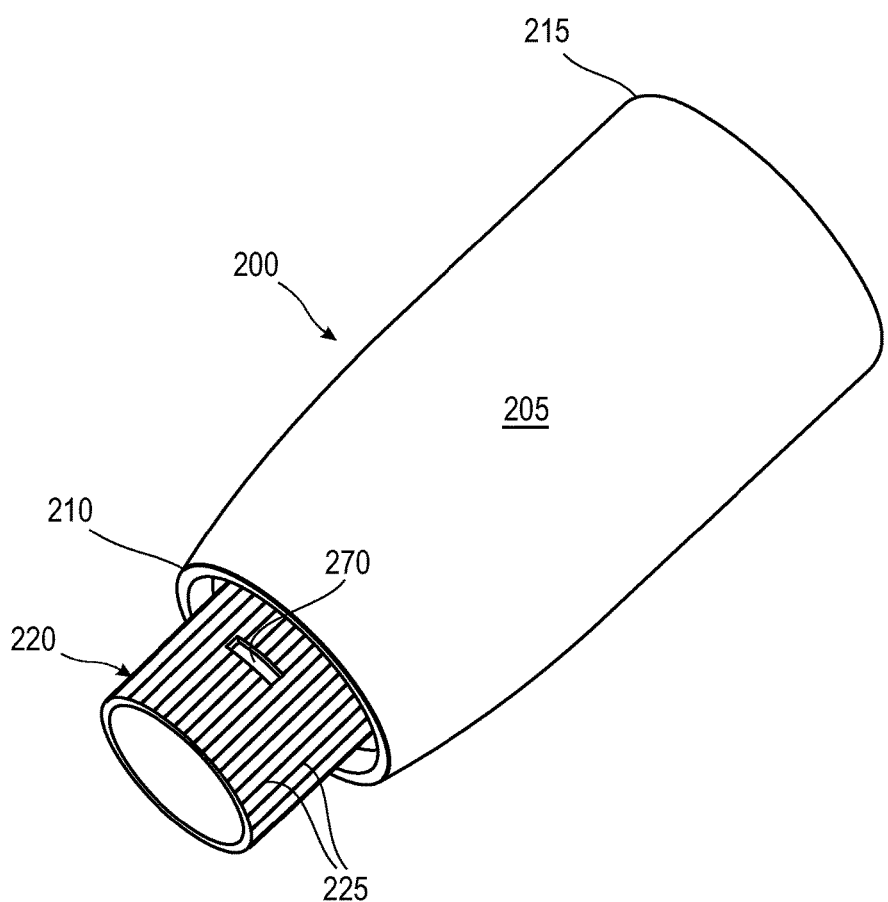
FIG. 4 shows another exemplary embodiment of a medicament delivery device with a delivery initiation indicator according to the present invention before use.

FIG. 4 shows another exemplary embodiment of a medicament delivery device 200 according to the present invention. The delivery device 200 may be any type of injection device which is used to inject a medicament from a syringe or cartridge. Those of skill in the art will understand that such injection devices include, but are not limited to, pen injectors, pre-filled syringes, autoinjectors, perfusion devices, infusion devices, etc.

In the exemplary embodiment shown in FIG. 4, the delivery device 200 includes a case 205 which may be a cylinder having an open distal end 210 and a proximal end. A trigger button may be coupled to the proximal end of the case 205 (or another area on the case 205) or the proximal end may be closed. Telescopically coupled to the case 205 may be a needle sleeve 220. The needle sleeve 220 may be biased (e.g., by a spring) in a first extended position relative to the case 205 to ensure that a needle on a syringe or cartridge in the delivery device 200 is covered prior to use. In the first extended position, a distal end of the needle sleeve 220 extends a first predetermined length beyond the distal end 210 of the case 205. In an exemplary embodiment, the first predetermined length includes a first indicia 225 such as, for example, a first color, a first symbol, a first text, a first graphic, etc. or any combination thereof. For example, the first indicia 225 may be the color green. When the needle sleeve 220 is in the first extended position, the first indicia 225 may be visible to a patient and indicate that the delivery device 200 has not been previously used and is ready for use.

As shown in the exemplary embodiment shown in FIG. 5A, the needle sleeve 220 is biased in the first extended position by a spring 235. A flange 240 on a proximal end of the needle sleeve 220 may abut a proximal portion of a rib 245 formed on the case 205 to prevent the needle sleeve 220 from moving distally relative to the case 205 under the biasing force of the spring 235 beyond the first extended position.

In the exemplary embodiment shown in FIG. 5A, an indicator sleeve 250 having a second indicia 230 may be telescopically disposed in the distal end 210 of the case 205. In an exemplary embodiment, the indicator sleeve 250 may be arranged radially between the case 205 and the needle sleeve 220. In an exemplary embodiment, the second indicia 230 may be, for example, a second color, a second symbol, a second text, a second graphic, etc. or any combination thereof. For example, the second indicia 225 may be the color red.

In an exemplary embodiment, the indicator sleeve 250 may include one or more first resilient latches 255 which, in a non-deflected position (shown in FIG. 5A), are adapted to engage one or more first notches 260 formed in the case 205, locking the indicator sleeve 250 in a retracted position relative to the case 205. The first latches 225 may be disposed on a proximal end of the indicator sleeve 250. In the retracted position, the indicator sleeve 250 is entirely contained within the case 205 and thus not visible to the patient. In a deflected position, the first latches 255 may deflect radially to disengage the first notches 260.

In an exemplary embodiment, the indicator sleeve 250 may include one or more second resilient latches 265 which, in a deflected position, are adapted to abut the needle sleeve 220. When the needle sleeve 220 translates in the proximal direction and one or more second notches 270 on the needle sleeve 220 align with the second latches 265, the second latches 265 transition to a non-deflected position and engage the second notches 270, locking the indicator sleeve 250 to the needle sleeve 220. The second latches 265 may be disposed on a distal end of the indicator sleeve 250. When the indicator sleeve 250 is locked to the needle sleeve 220, they will translate together. Thus, when the needle sleeve 220 is in a second extended position (e.g., after the delivery device 200 is removed from the injection site), the indicator sleeve 250 and the second indicia 230 will be visible to the patient.

Figure 6:
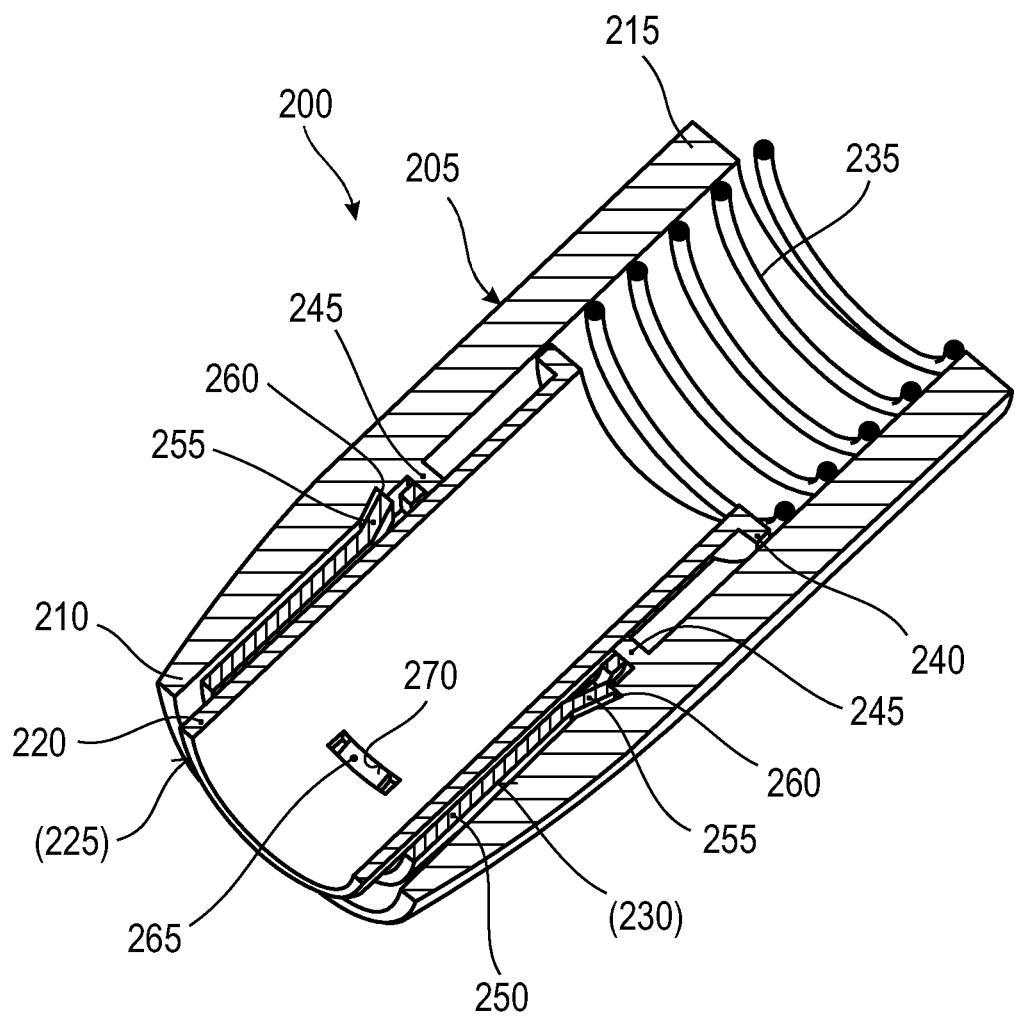
FIG. 6 shows another exemplary embodiment of a medicament delivery device with a delivery initiation indicator according to the present invention during use.

FIG. 6 shows another exemplary embodiment of the delivery device 200 during use. The delivery device 200 has been pressed against the injection site, causing the needle sleeve 220 to move from the first extended position to the retracted position against the biasing force of the spring 235. To the extent any frictional force between the needle sleeve 220 and the indicator sleeve 250 might cause the indicator sleeve 250 to translate in the proximal direction with the needle sleeve 220, a proximal end of the indicator sleeve 250 may abut a distal face of the rib 245. The rib 245 thus ensures that the indicator sleeve 220 does not translate relative to the needle sleeve 220 when the needle sleeve 220 moves from the first extended position to the retracted position.

When the needle sleeve 220 reaches the retracted position, the second notch 270 is aligned with the second latch 265, allowing the second latch 265 to deflect radially to the non-deflected position and engage the second notch 270.

Figure 7:
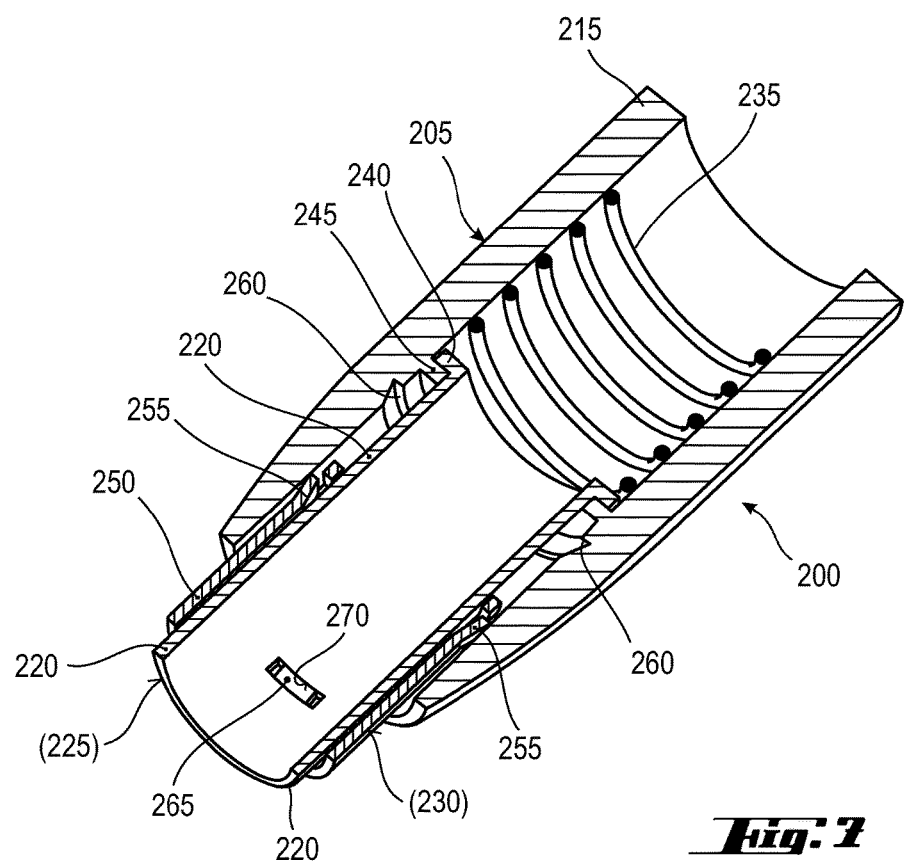
FIG. 7 shows another exemplary embodiment of a medicament delivery device with a delivery initiation indicator according to the present invention after use.

FIG. 7 shows another exemplary embodiment of the delivery device 200 after use. When the delivery device 200 is removed from the injection site, the biasing force of the spring 235 causes the needle sleeve 220 to translate distally relative to the case 205 from the retracted position to the second extended position. The biasing force of the spring 235 causes the first latch 255 to disengage the first notch 260. And, because the second latch 265 has engaged the second notch 270, the indicator sleeve 250 translates with the needle sleeve 220 from a retracted position to an extended position.

Figure 8:
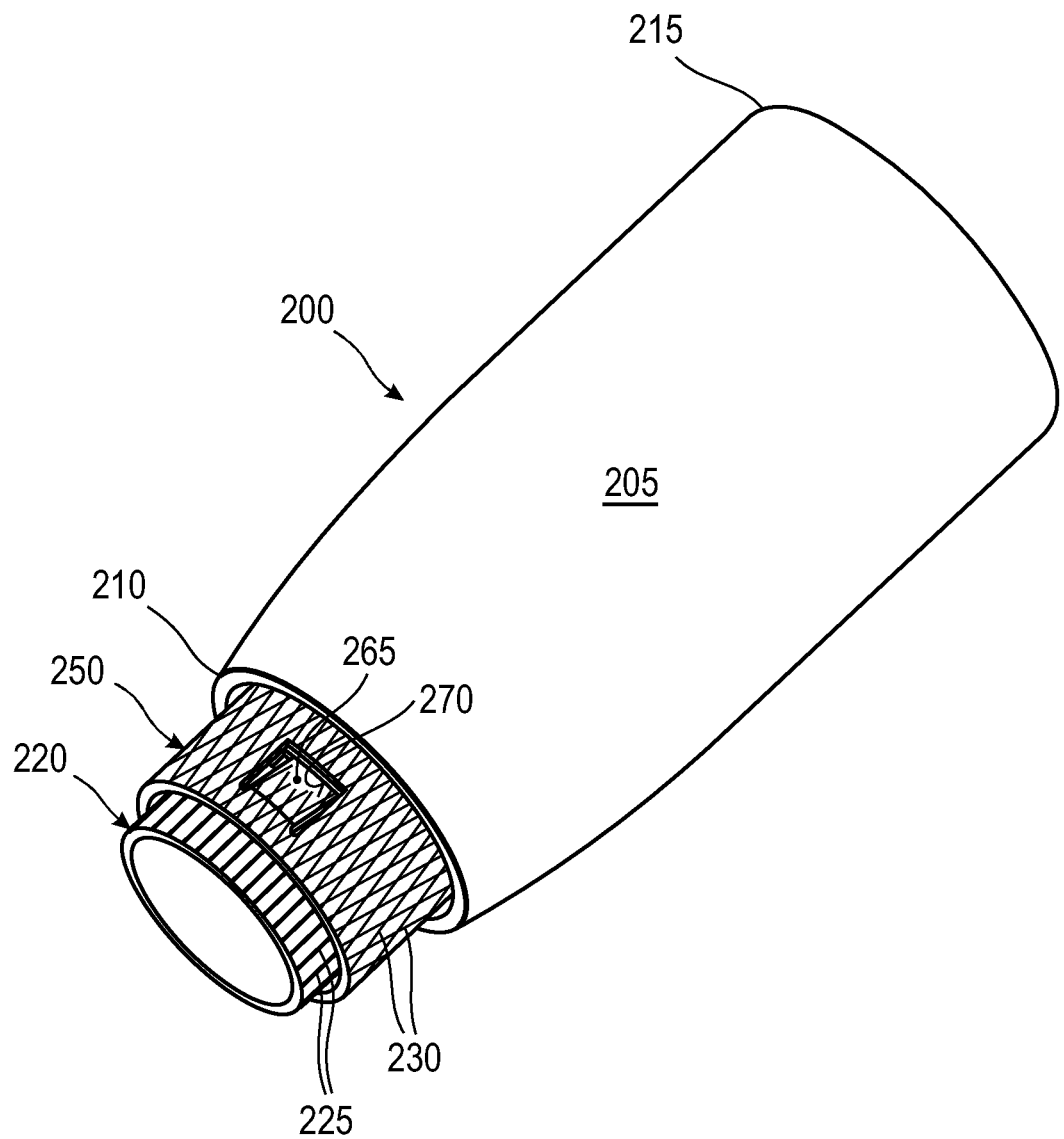
FIG. 8 shows another exemplary embodiment of a medicament delivery device with a delivery initiation indicator according to the present invention after use.

FIG. 8 shows another exemplary embodiment of the delivery device 200 after use. When the indicator sleeve 220 is in the extended position, the second indicia 230 is visible to the patient and thus provides a visual feedback that the delivery device 200 has been used and should not be reused.

Those of skill in the art will understand that modifications (additions and/or removals) of various components of the apparatuses, methods and/or systems and embodiments described herein may be made without departing from the full scope and spirit of the present invention, which encompass such modifications and any and all equivalents thereof.

The invention claimed is:

1. A medicament delivery device comprising:
   a case adapted to hold a container with a medicament, the container including a needle;
   a needle sleeve telescopically coupled to the case, the needle sleeve having a first extended position relative to the case in which the needle is covered, a retracted position relative to the case in which the needle is exposed, and a second extended position relative to the case in which the needle is covered;
   a first indicia disposed on the needle sleeve, wherein the first indicia is visible in the first extended position and the second extended position;
   a second indicia not visible in the first extended position and visible the second extended position; and
   an indicator sleeve telescopically disposed in the case, the indicator sleeve having a proximal position relative to the case in which the indicator sleeve is not visible and a distal position relative to the case in which the indicator sleeve is visible, wherein the indicator sleeve engages the needle sleeve when the needle sleeve is in the retracted position, and wherein the indicator sleeve translates from the proximal position to the distal position when the needle sleeve translates from the retracted position to the second extended position.

2. The medicament delivery device according to claim 1, wherein a distal end of the needle sleeve extends a first predetermined length beyond a distal end of the case in the first extended position and extends a second predetermined length beyond the distal end of the case in the second extended position, and wherein the second predetermined length is greater than the first predetermined length.

3. The medicament delivery device according to claim 2, wherein the first indicia is disposed on the first predetermined length of the needle sleeve, and the second indicia is disposed on the needle sleeve proximal of the first predetermined length.

4. The medicament delivery device according to claim 1, wherein the second indicia is disposed on the indicator sleeve.

5. The medicament delivery device according to claim 1, wherein the indicator sleeve includes one or more first resilient latches adapted to releasably engage one or more first notches in the case.

6. The medicament delivery device according to claim 5, wherein the indicator sleeve includes one or more second resilient latches adapted to engage one or more second notches in the needle sleeve.

7. The medicament delivery device according to claim 6, wherein the one or more second resilient latches engage the second notches when the needle sleeve is in the retracted position and the indicator sleeve is in the proximal position.

8. The medicament delivery device according to claim 7, wherein the one or more first resilient latches disengage the first notches when the needle sleeve translates from the retracted position to the second extended position and the indicator sleeve translates from the proximal position to the distal position.

9. The medicament delivery device according to claim 1, wherein a rib is disposed in the case to prevent proximal movement of the indicator sleeve from the proximal position.

10. The medicament delivery device according to claim 1, further comprising:
a spring biasing the needle sleeve away from the retracted position.

11. The medicament delivery device according to claim 1, wherein the first indicia includes at least one of a first color, a first symbol, a first text and a first graphic, and the second indicia includes at least one of a second color, a second symbol, a second text and a second graphic.

12. The medicament delivery device according to claim 1, wherein the needle sleeve is locked in the second extended position.

13. A medicament delivery device comprising:
a case adapted to hold a container with a medicament, the container including a needle;
a needle sleeve telescopically coupled to the case, the needle sleeve having a first extended position relative to the case in which the needle is covered, a retracted position relative to the case in which the needle is exposed, and a second extended position relative to the case in which the needle is covered;
an indicia invisible prior to the medicament delivery device being used and visible after the medicament delivery device has been used; and
an indicator sleeve telescopically disposed in the case, the indicator sleeve having a proximal position relative to the case in which the indicator sleeve is not visible and a distal position relative to the case in which the indicator sleeve is visible, wherein the indicator sleeve engages the needle sleeve when the needle sleeve is in the retracted position, and wherein the indicator sleeve translates from the proximal position to the distal position when the needle sleeve translates from the retracted position to the second extended position.

14. The medicament delivery device according to claim 13, wherein the indicia is a second indicia, and wherein the medicament delivery device further comprises a first indicia disposed on the needle sleeve, wherein the first indicia is visible prior to the medicament delivery device being used and after the medicament delivery device has been used.

15. The medicament delivery device according to claim 14, wherein the first indicia is formed on the needle sleeve and the second indicia is formed on the indicator sleeve disposed in a distal end of the case and arranged radially between the case and the needle sleeve.

16. The medicament delivery device according to claim 14, wherein the first indicia is visible in the first extended position and the second extended position.

17. The medicament delivery device according to claim 16, wherein a distal end of the needle sleeve extends a first predetermined length beyond a distal end of the case in the first extended position and extends a second predetermined length beyond the distal end of the case in the second extended position, and wherein the second predetermined length is greater than the first predetermined length.

18. The medicament delivery device according to claim 13, wherein the indicia is not visible in the first extended position and is visible in the second extended position.

* * * * *

UNITED STATES PATENT AND TRADEMARK OFFICE
CERTIFICATE OF CORRECTION

PATENT NO. : 10,173,017 B2
APPLICATION NO. : 14/435564
DATED : January 8, 2019
INVENTOR(S) : Stephan Riedel et al.

Page 1 of 1

It is certified that error appears in the above-identified patent and that said Letters Patent is hereby corrected as shown below:

On the Title Page

On page 2, Column 1, Line 5 (approx.) (Abstract), delete "visible the second extended position" and insert -- visible in the second extended position --

In the Specification

In Column 1, Line 6 (approx.), delete "Nos." and insert -- No. --

In the Claims

In Column 10, Line 24 (Claim 1), delete "visible the second extended position" and insert -- visible in the second extended position --

Signed and Sealed this
Eighteenth Day of June, 2019

Andrei Iancu
*Director of the United States Patent and Trademark Office*